(12) United States Patent
Deguchi et al.

(10) Patent No.: US 11,685,705 B2
(45) Date of Patent: *Jun. 27, 2023

(54) METHOD FOR PRODUCING α-ALLYLATED CYCLOALKANONE

(71) Applicant: Kao Corporation, Tokyo (JP)

(72) Inventors: Jun Deguchi, Tokyo (JP); Makoto Sakakibara, Wakayama (JP); Daichi Sakoda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/440,564

(22) PCT Filed: Mar. 17, 2020

(86) PCT No.: PCT/JP2020/011667
§ 371 (c)(1),
(2) Date: Sep. 17, 2021

(87) PCT Pub. No.: WO2020/189670
PCT Pub. Date: Sep. 24, 2020

(65) Prior Publication Data
US 2022/0153672 A1    May 19, 2022

(30) Foreign Application Priority Data

Mar. 18, 2019  (JP) .................................. 2019-049617

(51) Int. Cl.
*C07C 45/65* (2006.01)
*C07C 45/51* (2006.01)
*C07C 45/66* (2006.01)

(52) U.S. Cl.
CPC .......... *C07C 45/515* (2013.01); *C07C 45/513* (2013.01); *C07C 45/66* (2013.01); *C07C 2601/20* (2017.05)

(58) Field of Classification Search
CPC ...... C07C 45/513; C07C 45/515; C07C 45/66
See application file for complete search history.

(56) References Cited

U.S. PATENT DOCUMENTS

| | | | |
|---|---|---|---|
| 4,335,262 | A | 6/1982 | Schulte-Elte et al. |
| 4,480,107 | A | 10/1984 | Schulte-Elte et al. |
| 10,087,129 | B2 | 10/2018 | Tanino et al. |
| 2010/0016308 | A1 | 1/2010 | Burkamp et al. |
| 2012/0088935 | A1 | 4/2012 | Schelper et al. |
| 2016/0031783 | A1 | 2/2016 | Micoine et al. |
| 2017/0362153 | A1 | 12/2017 | Tanino et al. |
| 2018/0346478 | A1 | 12/2018 | Werner et al. |

FOREIGN PATENT DOCUMENTS

| | | |
|---|---|---|
| CN | 107001214 A | 8/2017 |
| CN | 108290901 A | 7/2018 |

(Continued)

OTHER PUBLICATIONS

International Search Report dated Jun. 9, 2020 in PCT/JP2020/011667 filed Mar. 17, 2020, 4 pages.

(Continued)

*Primary Examiner* — Sikarl A Witherspoon
(74) *Attorney, Agent, or Firm* — Oblon, McClelland, Maier & Neustadt, L.L.P.

(57) ABSTRACT

Provided is a method with which an α-allylated cycloalkanone is obtained from a macroyclic compound used as a starting material. The method is a method for producing an α-allylated cycloalkanone represented by General Formula (IV), and the method includes a step of reacting a compound represented by General Formula (I) and/or a compound represented by General Formula (II) with a compound represented by General Formula (III) in the presence of an acid catalyst to produce an α-allylated cycloalkanone represented by General Formula (IV), the acid catalyst including an acid catalyst that includes an ammonium cation and an anion.

[Chemical Formula 1]

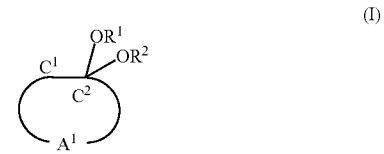

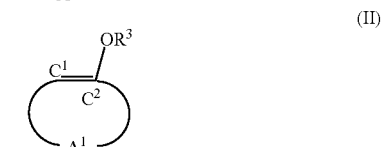

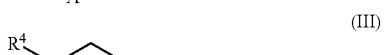

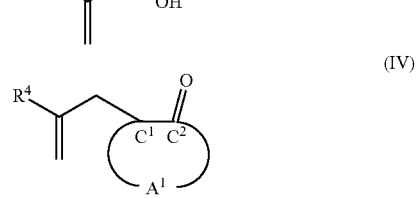

where $R^1$, $R^2$, and $R^3$ are the same or different and each of them is an alky group having 1 or mom and 4 or less of carbon atoms, the group -$A^1$- (it should be noted that the front bond refers to a bond that binds to the carbon atom $C^1$ and the back bond refers to a bond that binds to the carbon atom $C^2$) is an alkylene group having 4 or more and 20 or les of carbon atoms that optionally contains a hetero atom and optionally has a substituent, and $R^4$ is a hydrogen atom or an alkyl group having 1 or more and 4 or less of carbon atoms.

17 Claims, No Drawings

(56) References Cited

FOREIGN PATENT DOCUMENTS

| | | | |
|---|---|---|---|
| DE | 29 16 418 A1 | 11/1980 | |
| DE | 197 02 279 A1 | 7/1998 | |
| FR | 2 645 530 A1 | 10/1990 | |
| GB | 1 205 047 | 9/1970 | |
| GB | 2 125 397 A | 3/1984 | |
| JP | 51-29147 A | 8/1976 | |
| JP | 56-46881 A | 4/1981 | |
| JP | 63-2946 A | 1/1988 | |
| JP | 2002-105010 A | 4/2002 | |
| JP | 2009-515864 A | 4/2009 | |
| JP | 2010-95447 A | 4/2010 | |
| JP | 2014-500237 A | 1/2014 | |
| JP | 2015-533799 A | 11/2015 | |
| JP | 2016-34937 A | 3/2016 | |
| JP | 2016-124867 A | 7/2016 | |
| JP | 2017-505835 A1 | 2/2017 | |
| JP | 2017-122101 A | 7/2017 | |
| WO | WO 2011/073843 A1 | 6/2011 | |
| WO | WO2012/045786 A | 4/2012 | |
| WO | WO 2015/036402 A1 | 3/2015 | |
| WO | WO 2015/107017 A1 | 7/2015 | |
| WO | WO 2017/089327 A1 | 6/2017 | |
| WO | WO 2018/011386 A1 | 1/2018 | |
| WO | WO 2019/086207 A1 | 5/2019 | |

OTHER PUBLICATIONS

Howard. W.L., et al., *Organic Synthesis*, vol. 5, 1973, p. 14, 3 total pages.
Mansilla, H., et al., "Iron(III) Tosylate in the Preparation of Dimethyl and Diethyl Acetals from Ketones and β-Keto Enol Ethers from Cyclic β-Diketones", *Synthetic Communications*, vol. 38, 2008, pp. 2607-2618, 13 total pages.
Terent'Ev, A.O., et al., "New transformation of cycloalkanone acetals by peracids α,ω-dicarboxylic acids synthesis", Central European Journal of Chemistry, vol. 3, 2005, pp. 417-431.
Cardinale, G., et al., "Bifunctional Compounds From Reactions of Alkoxy Hydroperoxides With Metal Salts", Tetrahedron, vol. 41, No. 24, 1985. pp. 6051-6054.
Gardi, R., et al., "Alkylation of steroids by the Claisen rearrangement of allyl ethers. II. Rearrangement of 17-oxo steroid enol ethers", Gazzetta Chimica Italiana, vol. 95, No. 4, 1965, pp. 351-367.
Organic synthesis II—alcohol, amine-), The Chemical Society of Japan, 1992, pp. 245-258, 20 total pages (with English Translation).
Dubs, P., et al., "Novel Synthesis of a [10] (2,6)Pyridinophane, a Structural Isomer of Muscopyridine", J.C.S. Chem, Comm., 1976, p. 1021.
Whol. R.A., "A Convenient One-Step Procedure for the Synthesis of Cyclic Enol Ethers. The Preparation of 1-Methoxy-1-cycloalkenes", Syntheses, 1974, pp. 38-40.
Rautenstrauch, V., et al., "92. A Short Synthesis of (±)-Muscone", Helvetica Chimica Acta, vol. 73, 1990, pp. 896-901.
Sugiura, M., et al., "Regiochemical Control in the Pd(II)-Catalyzed Claisen Rearrangement via In Situ Enol Ether Exchange", Tetrahedron Letters, vol. 37, No. 44, 1996, pp. 7991-7994.
Cresson, P., et al., "α-alkylation of lactams by Claisen rearrangement of 0-unsaturated enolates", C.R. Acad. SC, Serie C, vol. 275, 1972, pp. 1299-1300.
Database CASREACT, AN 159:515223, Retrieved from STN international [online], 2007, 1 page.
Kasal, A., et al., "On Steroids. CXXXVII. Preparation of Some Cyclic Steroidal Ethers", Collection Czechoslov. Chem. Commun. vol. 34, 1969, pp. 3479-3496.
Daub, G.W., et al., "Ketal Claisen Rearrangement of Simple Aliphatic Ketals", *J. Org. Chem.* vol. 48, No. 22, 1983, pp. 3876-3883.
Raucher, S., et al., "Indole Alkaloid Synthesis via Claisen Rearrangement. Total Synthesis of Secodine", *J. Am. Chem. Sec.*, vol. 103, No. 9, 1981, pp. 2419-2421.
Daub, G.W., et al., "The Steroselectivity of Ketal Claisen Rearrangements With Ketals of Simple Cyclic Ketones", Tetrahedron Letters, vol. 27, No. 52, 1986, pp. 6311-6314.
International Search report dated Dec. 10, 2019 in PCT/JP2019/036991 filed Sep. 20, 2019, 2 pages.
Rohanna, J.C., et al., "Olefinic-Lactone Cyclizations to Marcocycles", Organic Letters, vol. 11, No. 2, 2009, pp. 493-495.
U.S. Appl. No. 17/280,680, filed Mar. 26, 2021, Yuki Kashiwagi.
Raymond P. Lutz, "Catalysis of the Cope and Claisen Rearrangements", Chemical Reviews, Jun. 1984, vol. 84, No. 3, 43 pages.
Combined Chinese Office Action and Search Report dated Jul. 7, 2021 in corresponding Chinese Patent Application No. 201980062975.8 (with English Translation and English Translation of Category of Cited Documents), 10 pages.
Extended European Search Report dated May 20, 2022, in corresponding European Patent Application No. 19866843.6, 7 pages.
Ohloff, G., Becker, J. and Schulte-Elte, K.H. (1967), "Synthese von Exalton und racemischem Muscon aus Cyclododecanon" Vorlaeufige Mitteilung. HCA, 50: 705-708.
Knopff, O., and J. Kuhne. "New Practical Synthesis of the Exceptional Musk Odorants (R)- Muscone and (R,Z)-5-Muscenone", CHIMIA, vol. 62, No. 6, Jun. 2008, pp. 489-492, doi: 10-2533/chimia.2008.489.
Fehr, C., Galindo, J. and Etter, O. (2004), "An Efficient Enantioselective Sysnthesis of (+)-(R,Z)-5-Muscenone and (−)-(R)-Muscone— An Example of a Kinetic Resolution and Enantioconvergent-Transformation", Eur.J. Org. Chem., 2004: 1953-1957.
Office Action dated Oct. 6, 2022, in corresponding Israeli Patent Application No. 286631.

METHOD FOR PRODUCING α-ALLYLATED CYCLOALKANONE

TECHNICAL FIELD

The present invention relates to a method for producing an α-allylated cycloalkanone represented by General Formula (V).

BACKGROUND ART

Macrocyclic compounds are known to exhibit activity useful in the fields of pharmaceutical drugs, perfume, agricultural chemicals, and the like. Muscenone, which is one type of macrocyclic ketone, is a highly biodegradable perfume material with high scent persistence and elegant feel. In order to meet increasing needs of easily degradable synthetic musk materials in recent years, there is demand for the development of a safe and highly efficient production method.

[Chemical Formula 1]

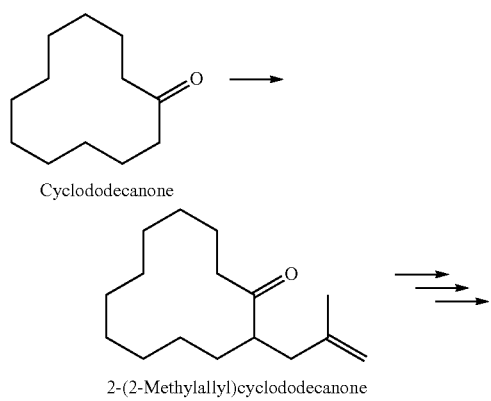

Cyclododecanone 2-(2-Methylallyl)cyclododecanone

Muscenone

Muscenone can be obtained using a method including a step of allylating the α-site of cyclododecanone to obtain 2-(2-methylallyl)cyclododecanone and several steps of converting 2-(2-methylallyl)cyclododecanone. The following method is reported as the method for allylating the α-site of cyclododecanone. That is, cyclododecanone and methallyl chloride are reacted to obtain 2-(2-methylallyl)cyclododecanone in one step (Patent Document 1).

[Chemical Formula 2]

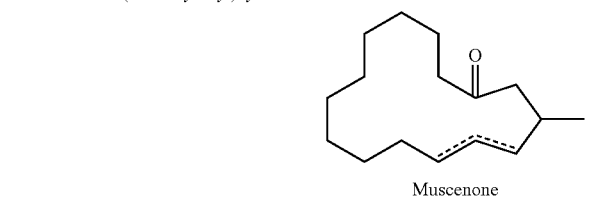

Cyclododecanone

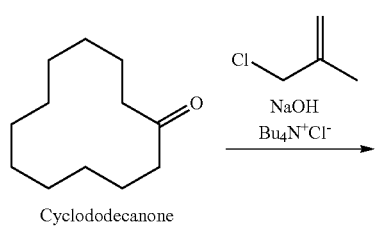

Cyclododecanone

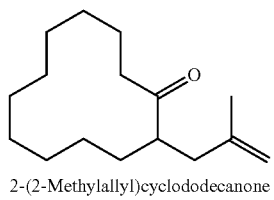

2-(2-Methylallyl)cyclododecanone

A method is also reported in which 1,1-dimetoxycyclododecane is reacted with crotyl alcohol in the presence of propionic acid to produce 2-(1-methylaryl)cyclododecanone (Patent Document 2).

[Chemical Formula 3]

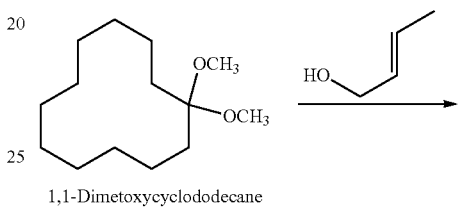

1,1-Dimetoxycyclododecane

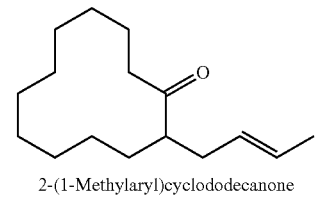

2-(1-Methylaryl)cyclododecanone

Moreover, a reaction for introducing an allyl group to the α-site of a cyclic ketone that is not a macrocyclic compound is reported (Patent Document 3, Non-Patent Document 1).

[Chemical Formula 4]

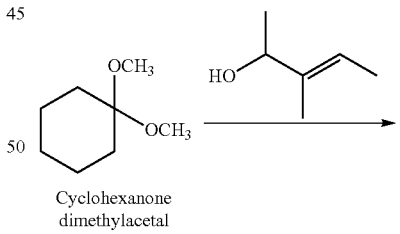

Cyclohexanone dimethylacetal

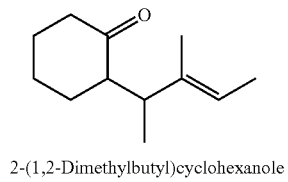

2-(1,2-Dimethylbutyl)cyclohexanole

Furthermore, a reaction for producing 2-allylcyclohexanone by heating cyclohexanone diallylacetal in the presence of p-toluenesulfonic acid is reported (Non-Patent Document 1).

[Chemical Formula 5]

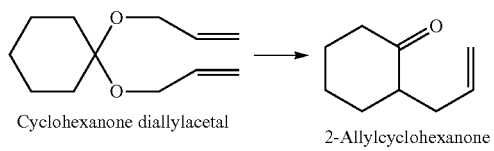

Cyclohexanone diallylacetal → 2-Allylcyclohexanone

CITATION LIST

Patent Documents

Patent Document 1: German Patent No. 2916418
Patent Document 2: JP 2015-533799A
Patent Document 3: WO 2011/073843

Non-Patent Document

Non-Patent Document 1: W. L. Howard, N. B. Lorette, Organic Synthesis, Vol. 5, 1973, p. 14

DISCLOSURE OF INVENTION

Problem to be Solved by the Invention

It is known that cycloalkanone dialkylacetals as starting materials are reacted in the presence of various acids in order to produce α-allylated cycloalkanones instead of allylating the α-sites of cycloalkanones as mentioned above. However, a method has not been known with which a highly pure α-allylated cycloalkanone is obtained in increased yield.

It is an object of the present invention to provide a method with which a highly pure α-allylated cycloalkanone is obtained in increased yield from a cyclic compound cycloalkanone dialkylacetal body or an alkoxy vinyl ether body used as a starting material.

Means for Solving Problem

Surprisingly, the inventors of the present invention found that, when a cycloalkanone dialkylacetal body and/or an alkoxy vinyl ether body were reacted with allyl alcohol in the presence of a specific acid catalyst, a highly pure α-allylated cycloalkanone was obtained in increased yield.

That is, the present invention is directed to a method for producing a compound represented by General Formula (IV) below (also referred to as a "compound of Formula V)" or a "compound (IV)" hereinafter), and the method includes:

a step of reacting a compound represented by General Formula (I) (cycloalkanone dialkylacetal body) (also referred to as a "compound of Formula (I)" or a "compound (I)" hereinafter) and/or a compound represented by General Formula (II) (alkoxy vinyl ether body) (also referred to as a "compound of Formula (II)" or a "compound (II)" hereinafter) with a compound represented by General Formula (III) (also referred to as a "compound of Formula (III)" or a "compound (III)" hereinafter) in the presence of an acid catalyst to produce an α-allylated cycloalkanone represented by General Formula (IV) (also referred to as a "compound of Formula (IV)" or a "compound (IV)" hereinafter), wherein the acid catalyst includes an acid catalyst that consists of an ammonium cation and an anion.

[Chemical Formula 6]

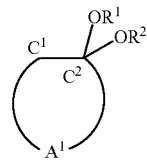 (I)

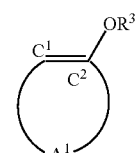 (II)

(III)

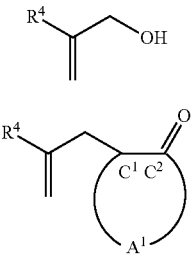 (IV)

In the formulae above, $R^1$, $R^2$, and $R^3$ are the same or different and each of them is an alkyl group having 1 or more and 4 or less of carbon atoms, the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

In the above-mentioned step, the compound of Formula (IV) can be obtained through acetal exchange between acetal moieties ($OR^1$, $OR^2$, $OR^3$) of the compound of Formula (I) and/or the compound of Formula (II) and the compound of Formula (III), and subsequent Claisen rearrangement.

Also, the present invention is directed to the method for producing a compound of Formula (IV), which further includes a step of reacting a compound represented by General Formula (V) (also referred to as a "compound of Formula (V)" or a "compound (V)" hereinafter) with alcohol having 1 or more and 4 or less of carbon atoms in the presence of a second acid catalyst to produce the compound of Formula (I) (cycloalkanone dialkylacetal body) and/or the compound of Formula (II) (alkoxy vinyl ether body).

[Chemical Formula 7]

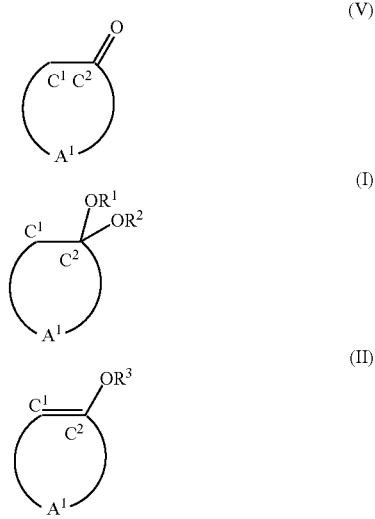

In the formulae above, $R^1$, $R^2$, and $R^3$ are the same or different and each of them is an alkyl group having 1 or more and 4 or less of carbon atoms, and the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent.

Effects of the Invention

With the present invention, it is possible to obtain an α-allylated cycloalkanone in increased yield and a highly pure product in increased yield from a cyclic compound cycloalkanone dialkylacetal body or an alkoxy vinyl ether body used as a starting material.

DISCLOSURE OF INVENTION

In the specification of the present application, "muscenone" is perfume manufactured by Firmenich SA (Geneva, Switzerland), which is a racemic mixture of various isomers. Specifically, muscenone is mainly a generic name for a mixture of Z-3-methyl-cyclopentadec-5-en-1-one, E-3-methyl-cyclopentadec-5-en-1-one, E-3-methyl-cyclopentadec-4-en-1-one, and Z-3-methyl-cyclopentadec-4-en-1-one.

Compound of Formula (I), Compound of Formula (II), Compound of Formula (III), Compound of Formula (IV), and Compound of Formula (V)

In Formula (I), Formula (IU, Formula (IV), and Formula (V) above, the "alkylene group having 4 or more and 20 or less of carbon atoms" in the "alkylene group having 4 or more and 20 or less of carbon atoms that optionally contains a hetero atom and optionally has a substituent" that corresponds to the group -$A^1$- is represented as a group —$(CH_2)_4$—, a group —$(CH_2)_5$—, a group —$(CH_2)_6$—, a group —$(CH_2)_7$—, a group —$(CH_2)_8$—, a group —$(CH_2)_9$—, a group —$(CH_2)_{10}$—, a group —$(CH_2)_{11}$—, a group —$(CH_2)_{12}$—, a group —$(CH_2)_{13}$—, a group —$(CH_2)_{14}$—, a group —$(CH_2)_{15}$—, a group —$(CH_2)_{16}$—, a group —$(CH_2)_{17}$—, a group —$(CH_2)_{18}$—, a group —$(CH_2)_{19}$—, or a group —$(CH_2)_{20}$—. From the viewpoint that the obtained compound of General Formula (I) is used as a precursor of a perfume compound, the "alkylene group having 4 or more and 20 or less of carbon atoms" is preferably alkylene having 6 or more and 14 or less of carbon atoms, more preferably alkylene having 8 or more and 14 or less of carbon atoms, even more preferably alkylene having 10 or more and 14 or less of carbon atoms, and even more preferably alkylene having 10 or more and 12 or less of carbon atoms.

In Formula (I), Formula (II), Formula (IV), and Formula (V), the "alkylene group having 4 or more and 20 or less of carbon atoms that optionally contains a hetero atom" in the "alkylene group having 4 or more and 20 or less of carbon atoms that optionally contains a hetero atom and optionally has a substituent" that corresponds to the group -$A^1$- may contain an oxygen atom, a nitrogen atom, and/or a sulfur atom as the hetero atom. That is, the "alkylene group having 4 or more and 20 or less of carbon atoms that optionally contains a hetero atom" is an alkylene group having 4 or more and 20 or less of carbon atoms that optionally contains one or more of an ether bond (—O—), an ester bond (—C(=O)—O— or —O—C(=O)—), and a thioether group (—S—), which do not inhibit the reaction. Examples of the above-mentioned "alkylene group having 4 or more and 20 or less of carbon atoms that optionally further contains one or more of an ether bond, an ester bond, and a thioether group" include a group —$(CH_2)_2$—O—$(CH_2)_2$—, a group —$(CH_2)_2$—O—$(CH_2)_6$—, a group —$(CH_2)_3$—O—$(CH_2)_5$—, a group —$(CH_2)_4$—O—$(CH_2)_4$—, a group —$(CH_2)_2$—O—$(CH_2)_7$—, a group —$(CH_2)_3$—O—$(CH_2)_6$—, a group —$(CH_2)O$—$(CH_2)_5$—, a group —$(CH_2)$—O—$(CH_2)_9$—, a group —$(CH_2)$—O—$(CH_2)_8$—, a group —$(CH_2)_3$—O—$(CH_2)_7$—, a group —$(CH_2)_4$—O—$(CH_2)_6$—, a group —$(CH_2)_5$—O—$(CH_2)_5$—, and a group —$(CH_{02})NH$—$(CH_2)_2$—, and, from the viewpoint that the obtained compound of General Formula (IV) is used as a precursor of a perfume compound, the group —$(CH_2)$—O—$(CH_2)$—, the group —$(CH_2)_2$—O—$(CH_2)_8$—, the group —$(CH_2)_3$—O—$(CH_2)_7$—, the group —$(CH_2)_4$—O—$(CH_2)_6$—, and the group —$(CH_2)_6$—O—$(CH)_5$— are preferable.

The "alkylene group having 4 or more and 20 or less of carbon atoms that optionally contains a hetero atom and optionally has a substituent" that corresponds to the group -$A^1$- is an "alkylene group having 4 or more and 20 or less of carbon atoms that optionally contains a hetero atom" and that optionally has one or more, preferably one or two, substituents. Examples of the substituent include alkyl groups, alkoxy groups, alkoxycarbonyl groups, alkanoyl groups, aryl groups, aralkyl groups, aryloxy groups, acyloxy groups, a carboxy group, halogen atoms, carbocycles, and heterocycles. Alkyl groups, alkoxycarbonyl groups, and alkoxy groups are preferable, and alkyl groups are more preferable. It should be noted that, when the substituent is an alkyl group, the carbon atoms contained in the alkyl group are not contained in 4 or more and 20 or less of carbon atoms in the "alkylene group having 4 or more and 20 or less of carbon atoms that optionally contains a hetero atom".

Two or more of the substituents may be combined together to form a carbocycle or heterocycle together with atoms to which the substituents are attached.

In Formula (I) and Formula (II) above, $R^1$, $R^2$, and $R^3$ are the same or different and each of them is an alkyl group having 1 or more and 4 or less of carbon atoms. $R^1$, $R^2$, and $R^3$ each are preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint that acetal exchange between the compound represented by General Formula (I) and/or the compound represented by General Formula (II) and the compound represented by General Formula (III) is promoted, the Claisen rearrangement thereby progresses, and thus the yield of the compound represented by General Formula (IV) is increased.

In Formula (III) and Formula (IV) above, $R^4$ is a hydrogen atom or an alkyl group having 1 or more and 4 or less of carbon atoms. $R^4$ is preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint that $R^4$ contributes to the formation of a stable conformation during the Claisen rearrangement, resulting in an increase in the yield of the compound of General Formula (IV).

In the method of the present invention, the group -$A^1$- in Formula (I), Formula (II), and Formula (IV) is preferably alkylene having 6 or more and 14 or less of carbon atoms that optionally has a substituent, more preferably alkylene having 8 or more and 14 or less of carbon atoms that optionally has a substituent, even more preferably alkylene having 10 or more and 14 or less of carbon atoms that optionally has a substituent, and even more preferably alkylene having 10 or more and 12 or less of carbon atoms that optionally has a substituent.

The compounds represented by General Formula (V) above are represented by the following formulae, for example. From the viewpoint that the obtained compound of General Formula (IV) is used as a precursor of a perfume compound, the compound represented by Formula (vi), the compound represented by Formula (vii), the compound represented by Formula (viii), and the compound represented by Formula (ix) are preferable, and the compound represented by Formula (vii) and the compound represented by Formula (viii) are more preferable. The compound represented by Formula (vii) is cyclododecanone. It should be noted that the compound represented by Formula (vii) is a compound of Formula (V-1), which will be described later.

[Chemical Formula 8]

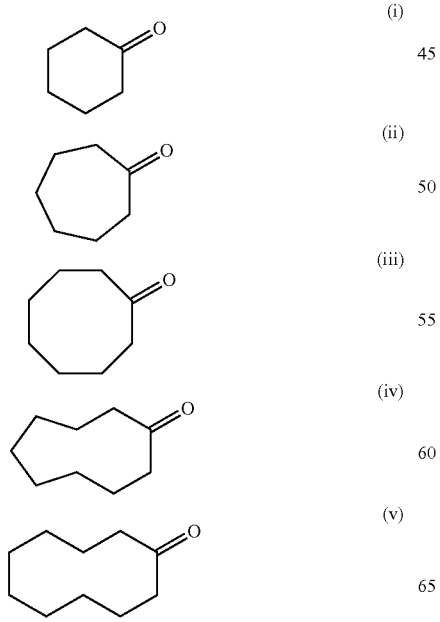
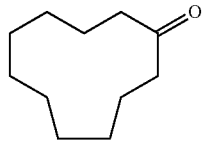
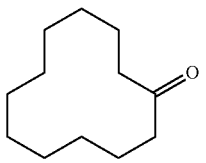
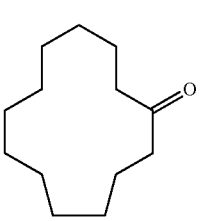
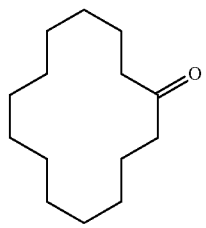

The compounds represented by General Formula (V) above are commercially available or can be obtained using a known method such as the method disclosed in JP 2016-34937A.

The compound represented by General Formula (I) above is 1,1-dimetoxycyclododecane, which is represented by Formula (7) below, or 1,1-diethoxycyclododecane, which is represented by Formula (17) below, for example. It should be noted that the compound represented by Formula (7) is a compound of Formula (I-1), which will be described later, and the compound represented by Formula (17) is a compound of Formula (I-2), which will be described later.

[Chemical Formula 9]

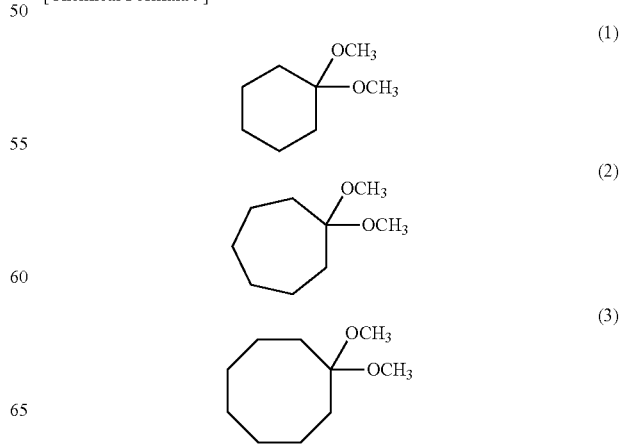

(4)
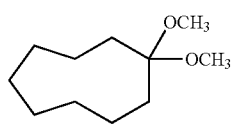

(5)
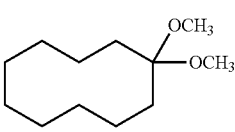

(6)
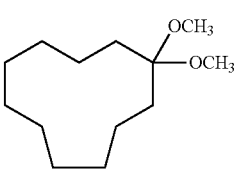

(7)
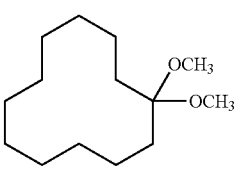

(8)
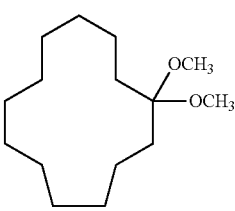

(9)
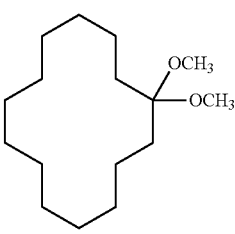

(11)
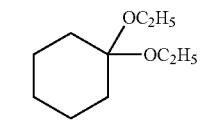

(12)
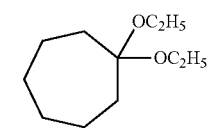

(13)
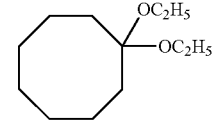

(14)
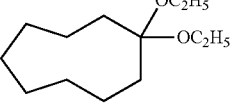

(15)
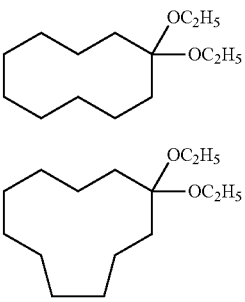

(16)
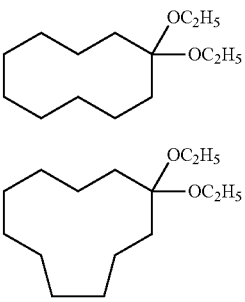

(17)
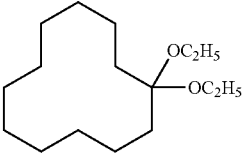

(18)
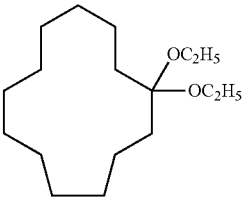

(19)
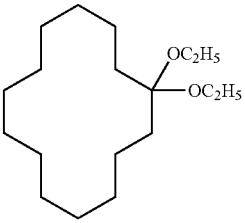

The compound represented by General Formula (II) above is 1-methoxy-1-cyclododecene, which is represented by Formula (37) below, or 1-ethoxy-1-cyclododecene, which is represented by Formula (47) below, for example. It should be noted that the compound represented by Formula (37) is a compound of Formula (II-1), which will be described later, and the compound represented by Formula (47) is a compound of Formula (II-2), which will be described later.

[Chemical Formula 10]

(31)
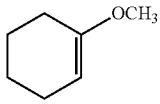

(32)
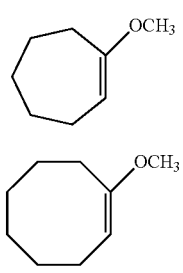

(33)
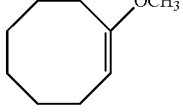

(34) 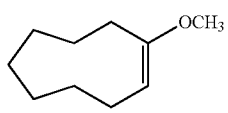

(35) 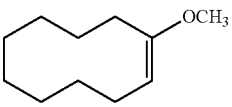

(36) 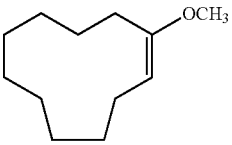

(37) 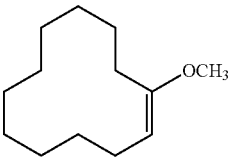

(38) 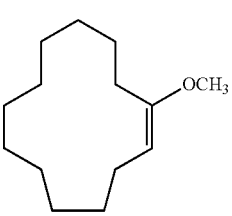

(39) 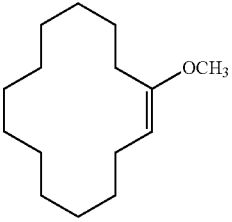

(41) 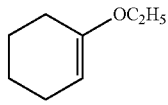

(42) 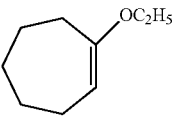

(43) 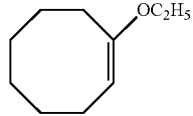

(44) 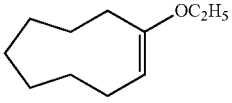

(45) 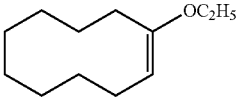

(46) 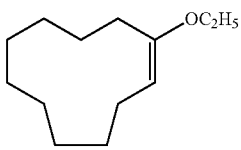

(47) 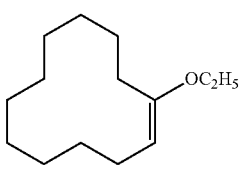

(48) 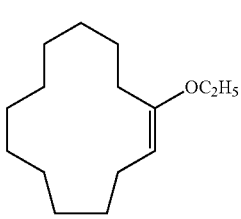

(49) 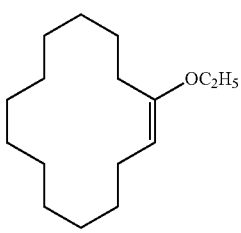

The compounds represented by General Formula (III) above are represented by the following formulae, for example. From the viewpoint that the obtained compound of General Formula (V) is used as a precursor of a perfume compound, 6-methallyl alcohol, which is represented by Formula (62) below, is preferable. The compounds represented by General Formula (III) above are commercially available or can be obtained using a known method such as the method disclosed in JP 2002-105010A. It should be noted that the compound represented by Formula (62) is a compound of Formula (III-1), which will be described later.

[Chemical Formula 11]

(61) 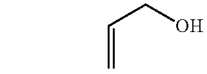

(62) 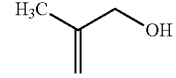

(63) 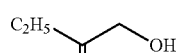

(64) 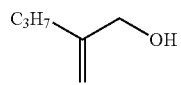

The compounds represented by General Formula (IV) above are represented by the following formulae, for example. From the viewpoint that the obtained compound of General Formula (IV) is used as a precursor of a perfume compound, the compound represented by Formula (xxvi), the compound represented by Formula (xxvii), the compound represented by Formula (xxviii), and the compound represented by Formula (xxix) are preferable, and the compound represented by Formula (xxvii) and the compound represented by Formula (xxviii) are more preferable. The compound represented by Formula (xxvii) is 2-(2-methylallyl)cyclododecanone. It should be noted that the compound represented by Formula (xxvii) is a compound of Formula (IV-1), which will be described later.

[Chemical Formula 12]

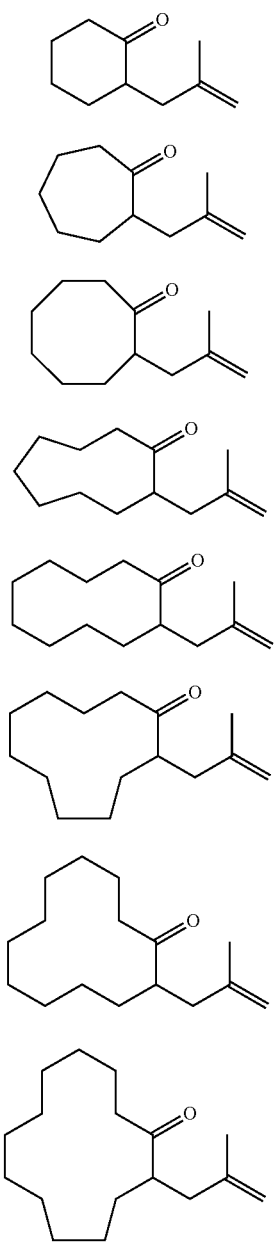

(xxi)
(xxii)
(xxiii)
(xxiv)
(xxv)
(xxvi)
(xxcii)
(xxviii)

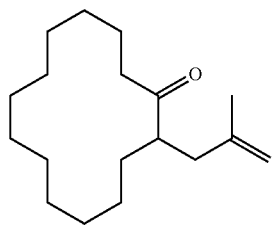

(xxix)

Step of Reacting Compound of Formula (I) and/or Compound of Formula (II) with Compound of Formula (III) in Presence of Acid Catalyst to Produce Compound of Formula (IV)

[Chemical Formula 13]

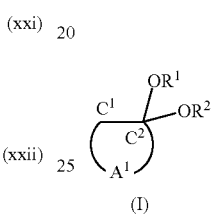

(I) and/or (II)

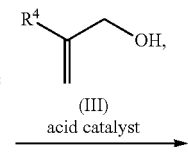

(III)
acid catalyst

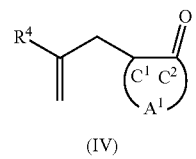

(IV)

In the formulae above, $R^1$, $R^2$, and $R^3$ are the same or different and each of them is an alkyl group having 1 or more and 4 or less of carbon atoms, the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

Acid Catalyst

In the present invention, the above-mentioned acid catalyst is an acid catalyst that consists of an ammonium cation and an anion. It is preferable that the ammonium cation is represented by General Formula (X) or Formula (XI).

[Chemical Formula 14]

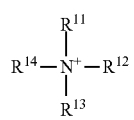

(X)

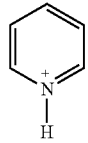

(XI)

In the formulae above, $R^{11}$, $R^{12}$, $R^{18}$, and $R^{14}$ are the same or different and each of them is a hydrogen atom or an alkyl group having 1 or more and 5 or less of carbon atoms.

In Formula (X) above, $R^{11}$, $R^{12}$, $R^{13}$, and $R^{14}$ each are preferably a hydrogen atom or an alkyl group having 1 or more and 3 or less of carbon atoms, more preferably a hydrogen atom, —$CH_3$, or —$C_2H_5$, even more preferably a hydrogen atom or —$CH_3$, and even more preferably a hydrogen atom, from the viewpoint of producing the compound of General Formula (IV) to be obtained in good yield.

It is preferable that the above-mentioned anion is a sulfonate anion represented by General Formula (XII) or a halide ion. The halide ion is preferably Cl⁻, Br⁻, or I⁻.

[Chemical Formula 15]

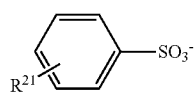

(XII)

In the formula above, $R^{21}$ is a hydrogen atom or an alkyl group having 1 or more 5 or less of carbon atoms.

In Formula (XII) above, $R^{21}$ is preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint that the compound (XII) is a relatively weak acid, volatilization of the compound (XII) is prevented even at high temperatures, isomerization of the compound of General Formula (III) is stably prevented, and the Claisen rearrangement is promoted. Furthermore, the substituent $R^{21}$ may be located at any of the ortho position, the meta position, and the para position relative to the "$SO_3^-$" group, and the para position is preferable.

It is preferable that one or more selected from p-toluenesulfonic acid, pyridinium p-toluenesulfonate, and ammonium chloride are contained as the acid catalyst.

In the present invention, the amount of the acid catalyst that is used is preferably $10^{-5}$ equivalents or more, more preferably $10^{-4}$ equivalents or more, and even more preferably $5\times10^{-4}$ equivalents or more, and is preferably 1 equivalent or less, more preferably 0.5 equivalents or less, and even more preferably 0.2 equivalents or less, relative to the total amount of the compound of General Formula (I) and the compound of General Formula (II). The reason for this is that, when the amount of the acid catalyst that is used is within the above-mentioned range, the reaction step can be performed while the isomerization of the compound of General Formula (II) is suppressed, and as a result, the Claisen rearrangement progresses in good yield. When the ammonium cation is represented by General Formula (X), the amount of the acid catalyst that is used is preferably 0.001 equivalents or more, more preferably 0.005 equivalents or more, and even more preferably 0.03 equivalents or more, and is preferably 1.0 equivalent or less, more preferably 0.5 equivalents or less, and even more preferably 0.1 equivalents or less. When the ammonium cation is represented by General Formula (XI), the amount of the acid catalyst that is used is preferably 0.0001 equivalents or more, more preferably 0.0005 equivalents or more, and even more preferably 0.0001 equivalents or more, and is preferably 0.1 equivalents or less, more preferably 0.05 equivalents or less, and even more preferably 0.01 equivalents or less.

Reaction Temperature

In the present invention, the step of reacting a compound represented by General Formula (I) and/or a compound represented by General Formula (II) with a compound represented by General Formula (III) in the presence of an acid catalyst to produce an α-allylated cycloalkanone represented by General Formula (IV) is performed at a temperature of 120° C. or higher, for example, preferably 125° C. or higher, or even more preferably 135° C. or higher, and 15000 or lower, for example, or preferably 145° C. or lower. The reason for this is that, when this step is performed at a temperature within this range, alcohol ($R^1OH$, $R^2OH$, $R^3OH$) resulting from acetal exchange between a compound represented by General Formula (I) and/or a compound represented by General Formula (II) and a compound represented by General Formula (III) can be volatilized to the outside of the reaction system, thus making it possible to accelerate the reaction.

Reaction Time

In the present invention, the reaction time of the step of reacting a compound of Formula (II) in the presence of the metal catalyst and the alcohol to produce a compound of Formula (I) is 2 hours to 5 days, for example, preferably 4 hours to 2 days, and more preferably 6 hours to 24 hours from the viewpoint of the production cost and production efficiency.

Reactor

In the present invention, it is preferable that the step of reacting a compound of Formula (I) and/or a compound of Formula (II) with a compound of Formula (III) in the presence of an acid catalyst to produce an α-allylated cycloalkanone represented by General Formula (IV) is performed using a rectification column.

In the method of the present invention, it is preferable that Formula (I) above is Formula (I-1) below, Formula (II) above is Formula (II-1) below, and Formula (V) above is Formula (IV-1) below. The reason for this is that the compound of Formula (IV-1) useful in a method for synthesizing muscenone, which will be described later, can be obtained.

[Chemical Formula 16]

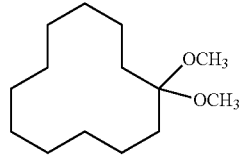

(I-1)

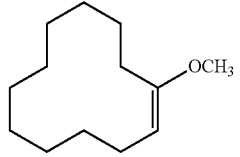

(II-1)

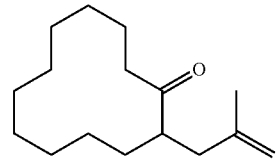

(IV-1)

Furthermore, the present invention is directed to a method for synthesizing muscenone in which the α-allylated cycloalkanone of Formula (IV-1) produced using the method mentioned above is used. Also, the present invention is directed to use of the α-allylated cycloalkanone of Formula (IV-1) as a raw material of muscenone.

[Chemical Formula 17]

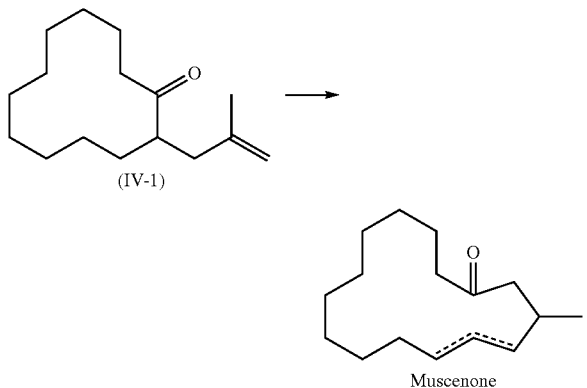

Specifically, the method for synthesizing muscenone includes the following steps:
(i) cyclization of the compound of Formula (IV-1);
(ii) hydrogenation;
(iii) oxidative cleavage;
(iv) reduction; and
(v) ring-opening.

[Chemical Formula 18]

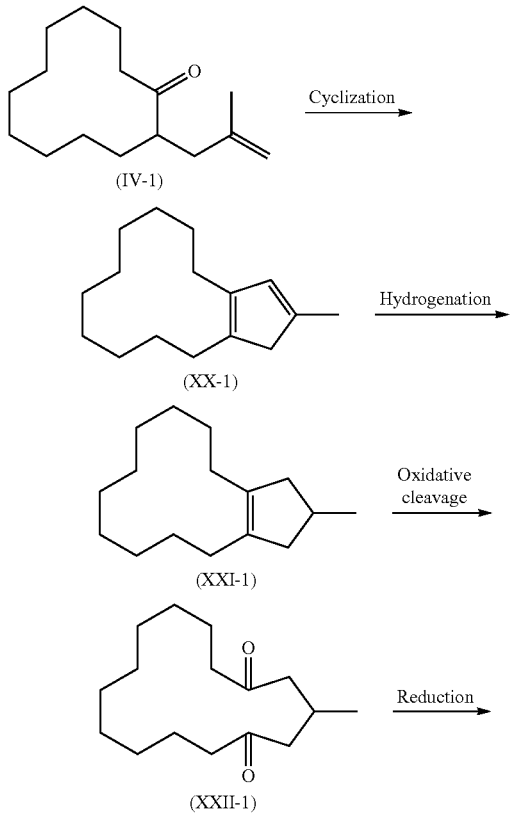

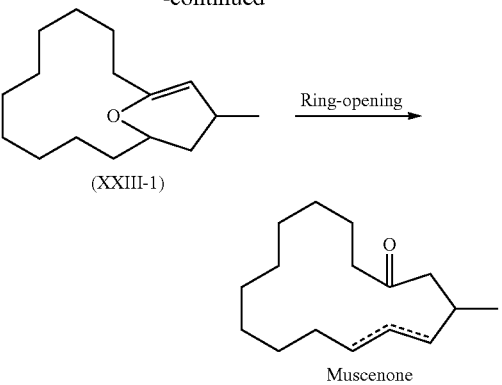

Step of Reacting Compound of Formula (V) with Alcohol Having 1 or more and 4 or less of Carbon Atoms in Presence of Second Acid Catalyst to Produce Compound of Formula (I) and/or Compound of Formula (II)

[Chemical Formula 19]

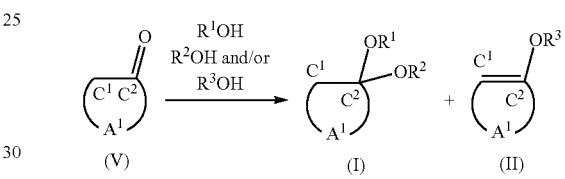

In the formulae above, $R^1$, $R^2$, and $R^3$ are the same or different and each of them is an alkyl group having 1 or more and 4 or less of carbon atoms, and the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent.

Alcohol

In the present invention, the above-mentioned alcohol is alcohol having 1 or more and 4 or less of carbon atoms. In the reaction formula above, the alcohol is represented as $R^1OH$, $R^2OH$, and/or $R^3OH$. The alcohol is preferably alkyl alcohol having 1 or more and 4 or less of carbon atoms. Examples of the alcohol include methanol, ethanol, 1-propanol, 1-butanol, and 2-methylpropanol.

Second Acid Catalyst

In the present invention, the second acid catalyst may be the same as or different from the acid catalyst used in the step of reacting a compound of Formula (I) and/or a compound of Formula (II) with a compound of Formula (III) in the presence of an acid catalyst to produce an α-allylated cycloalkanone of General Formula (IV). When these acid catalysts are different, examples of the second acid catalyst include p-toluenesulfonic acid, montmorillonite, and pyridinium p-toluenesulfonate, from the viewpoint that ketalization of the compound of Formula (V) is promoted. p-Toluenesulfonic acid or pyridinium p-toluenesulfonate is preferable.

In the present invention, the amount of the second acid catalyst that is used is preferably $10^{-5}$ equivalents or more, more preferably $10^{-4}$ equivalents or more, and even more preferably $5 \times 10^{-4}$ equivalents or more, and is preferably 1 equivalent or less, more preferably 0.5 equivalents or less, and even more preferably 0.2 equivalents or less, relative to the compound of Formula (V) above. The reason for this is that, when the amount of the second acid catalyst that is used is within the above-mentioned range, the second acid catalyst promotes the ketalization of the compound of Formula (V).

The above-mentioned step may also be performed in the presence of an orthocarboxylic ester in addition to the second acid catalyst. Examples of the orthocarboxylic ester include trimethylorthoformate and triethyl orthoformate.

Reaction Temperature

In the present invention, the step of reacting the compound of Formula (V) with alcohol having 1 or more and 4 or less of carbon atoms in the presence of the second acid catalyst to produce a compound of Formula (I) and/or a compound of Formula (II) is performed at a temperature of 120° C. or higher, for example, preferably 125° C. or higher, or more preferably 135° C. or higher, and 150° C. or lower, for example, or preferably 145° C. or lower. The reason for this is that, when this step is performed at a temperature within this range, the ketalization of the compound of Formula (V) is promoted.

Reaction Time

In the present invention, the reaction time of the step of reacting the compound of Formula (V) with alcohol having 1 or more and 4 or less of carbon atoms in the presence of the second acid catalyst to produce a compound of Formula (I) and/or a compound of Formula (II) is 2 hours to 5 days, for example, preferably 4 hours to 2 days, and more preferably 6 hours to 24 hours from the viewpoint of the production cost and production efficiency.

It should be noted that a compound of Formula (I) above and/or a compound of Formula (II) above can also be produced from a compound of Formula (V) using a known method such as the method disclosed in JP 2017-122101A.

Regarding the above-described embodiments, the present invention further discloses the following methods.

<1> A method for producing an α-allylated cycloalkanone represented by General Formula (V), including a step of reacting a compound represented by General Formula (I) and/or a compound represented by General Formula (II) with a compound represented by General Formula (III) in the presence of an acid catalyst to produce an α-allylated cycloalkanone represented by General Formula (IV), wherein the acid catalyst includes an acid catalyst that consists of an ammonium cation and an anion.

[Chemical Formula 20]

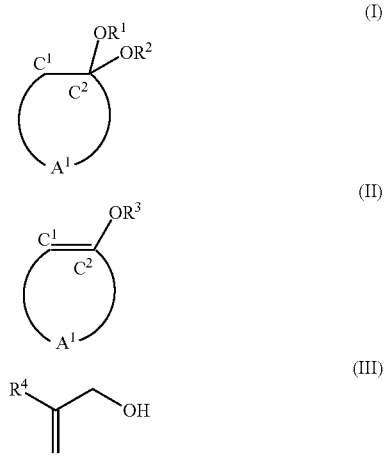

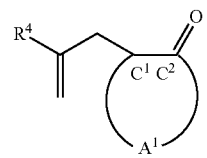

In the formulae above, $R^1$, $R^2$, and $R^3$ are the same or different and each of them is an alkyl group having 1 or more and 4 or less of carbon atoms, the group $-A^1-$ (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

<2> The method according to <1>, wherein the group $-A^1-$ is an alkylene group having 10 or more and 14 or less of carbon atoms that optionally has a substituent.

<3> The method according to <1> or <2>, wherein the ammonium cation is represented by General Formula 00 or Formula (XI).

[Chemical Formula 21]

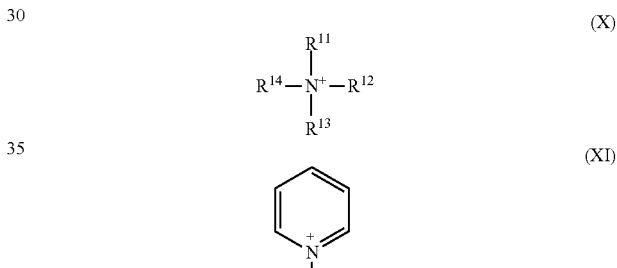

In the formulae above, $R^{11}$, $R^{12}$, $R^{13}$, and $R^{14}$ are the same or different and each of them is a hydrogen atom or an alkyl group having 1 or more and 5 or less of carbon atoms.

<4> The method according to any one of <1> to <3>, wherein the anion is a sulfonate anion represented by General Formula (XII) or a halide ion.

[Chemical Formula 22]

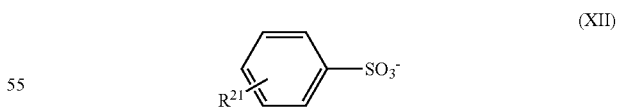

In the formula above, $R^{21}$ is a hydrogen atom or an alkyl group having 1 or more and 5 or less of carbon atoms.

<5> The method according to <4>, wherein the halide ion is $Cl^-$, $Br^-$, or $I^-$.

<6> The method according to any one of <1> to <5>, wherein the acid catalyst contains pyridinium p-toluenesulfonate or ammonium chloride.

<7> The method according to any one of <1> to <6>, wherein an amount of the acid catalyst that is used is $10^{-5}$ equivalents or more and 1 equivalent or less relative to a total amount of the compound represented by General Formula (I) and the compound represented by General Formula (II).

<8> The method according to anyone of <1> to <7>, wherein a reaction in the presence of the acid catalyst is performed at a temperature of 120° C. or higher and 145° C. or lower.

<9> The method according to any one of <1> to <8>, wherein the step is performed using a rectification column.

<10> The method according to any one of <1> to <9>, further including a step of reacting a compound represented by General Formula (V) with alcohol having 1 or more and 4 or less of carbon atoms in the presence of a second acid catalyst to produce the compound represented by General Formula (I) and/or the compound represented by General Formula (II).

[Chemical Formula 23]

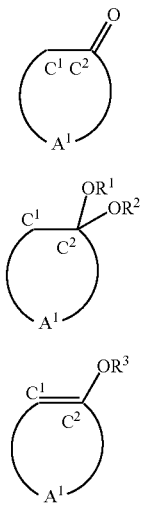

In the formulae above, $R^1$, $R^2$, and $R^3$ are the same or different and each of them is an alkyl group having 1 or more and 4 or less of carbon atoms, and the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent.

<11> The method according to <10>, wherein the second acid catalyst is constituted by one or two or more selected from p-toluenesulfonic acid, montmorillonite, and pyridinium p-toluenesulfonate.

<12> The method according to <10> or <11>, wherein a reaction in the presence of the second acid catalyst is performed at a temperature of 120° C. or higher and 145° C. or lower.

<13> The method according to any one of <10> to <12>, wherein the group -$A^1$- is an alkylene group having 10 or more and 14 or less of carbon atoms that optionally has a substituent.

<14> The method according to anyone of <1> to <13>, wherein the Formula (I) is Formula (I-1) below, the Formula (II) is Formula (II-1) below, and the Formula (IV) is Formula (IV-1) below.

[Chemical Formula 24]

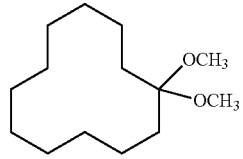

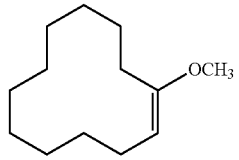

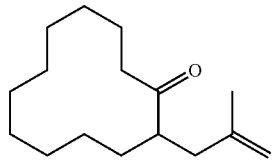

<15> A method for synthesizing muscenone in which an α-allylated cycloalkanone of Formula (IV 1) produced using the method according to <14> is used.

EXAMPLES

Gas Chromatography (GC) Apparatus and Analysis Conditions
GC apparatus: Model: GC-6850, manufactured by Agilent Technologies
Column: DB-1 (with an inner diameter of 0.25 mm, a length of 30 m, and a membrane thickness of 0.25 μm), manufactured by J&W
Carrier gas: He, 1.5 mL/min
Injection conditions: 300° C., split ratio of 100/1
Injection amount: 1 μL
Detection conditions: FID method, 300° C.
Column temperature conditions: 80° C.→rising the temperature at 10° C./minute→keeping the temperature at 300° C. for 10 minutes
Compound Identification
Compounds obtained in examples, experimental examples, and the like below were each compared with a commercially available product using GC (gas chromatography) or were each separately produced and isolated through column chromatography, followed by structure confirmation through NMR, IR, and GC-MS. The followings are manufacturers of the commercially available products and documents that were helpful to identify the structures.

1,1-Dimetoxycyclododecane (I-1): Palisandal (manufactured by Symrise AG: Product No. 690230, CAS No. 950-33-4)

1,1-Diethoxycyclododecane (I-2): Synthetic Communications, 2008, 38, 2607-2618 was used as a reference.

1-Methoxy-1-cyclododecene (II-1): Cent. Europ. J. Chem. 2005, 3, 417-431 was used as a reference.

1-Ethoxy-1-cyclododecene (II-2): Tetrahedron, 1985, 41, 6051-6054 was used as a reference.

2-(2-Methylallyl)cyclododecanone (IV-1): JP 2010-95447A was used as a reference.

The yield (%) was calculated using the following expression.

$$\text{Yield} = \frac{\text{Weight of reaction end solution} \times \dfrac{GC \text{ area \% of } 2-(2-\text{methylallyl})\text{cyclododecanone}}{236.4}}{\text{Feed amount of raw material} \times \dfrac{GC \text{ area \% of } 1,1-\text{dimethoxycyclo-dodecane}}{228.4} + \text{Feed amount of raw material} \times \dfrac{GC \text{ area \% of } 1-\text{methoxy}-1-\text{cyclododecene}}{196.3}} \times 100$$

[Mathematical Formula 1]

Here, a GC area % refers to a ratio of an output chart area of the component detected using GC to the entire area.

Production Example 1

Synthesis of Mixture of 1,1-Dimetoxycyclododecane (I-1) and 1-Methoxy-1-cyclododecene (II-1)

[Chemical Formula 25]

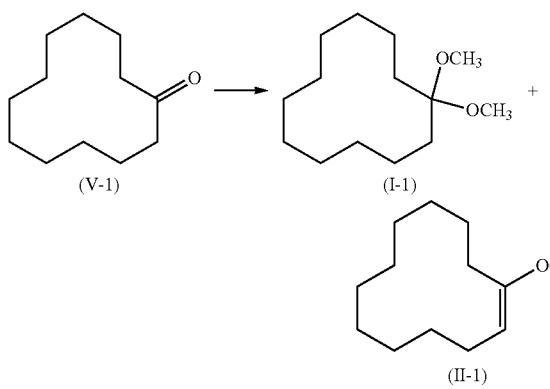

Cyclododecanone (V-1) (500.0 g, 2.743 mol), trimethyl orthoformate (349.5 g, 3.292 mol), and methanol (264.3 g, 8.229 mol) were placed into a 2-L four-neck flask and stirred at room temperature into a homogeneous solution. Pyridinium p-toluenesulfonate (PPTS, 0.7 g, 2.743 mmol) was added thereto, stirred, and dissolved. A thermometer, a mechanical stirrer, and a 10-step Sulzer rectification column (manufactured by Kyowa Chemical) were installed on the 2-L four-neck flask. Under a nitrogen atmosphere, stirring of the content in the 2-L four-neck flask was started at an outside temperature of 80° C. A reactant was sampled from the 2-L four-neck flask over time and subjected to GC analysis, and thus the conversion rate of cyclododecanone (V-1) was observed. The reaction was stopped 6 hours after the start of the reaction, and the reaction mixture was cooled. As a result of gas chromatography analysis on the reaction solution at the end of the reaction, the component composition was as follows: 1,1-dimethoxycyclododecane (I-1) corresponded to 93.1 GC area %, and 1-methoxy-1-cyclododecene (II-1) corresponded to 3.6 GC area %.

Next, methanol and trimethyl orthoformate contained in the product were distilled off under reduced pressure. AK-shaped pipe, a cooling pipe, and a distillate receiver were installed on the 2-L four-neck flask. Under a nitrogen atmosphere, distillation of the product under reduced pressure was started at an outside temperature of 110° C. The pressure was reduced from the ordinary pressure to 66.5 kPa one hour after the start of the distillation, and then the distillation under reduced pressure was continued. The flow of distillate into the receiver stopped in 2 hours, and the distillation under reduced pressure was finished. As a result of gas chromatography analysis on the reaction solution after the distillation, the component composition was as follows: 1,1-dimethoxycyclododecane (I-1) corresponded to 43.5 GC area %, and 1-methoxy-1-cyclododecene (II-1) corresponded to 54.5 GC area %.

Example 1

Synthesis of 2-(2-Methylallyl)cyclododecanone

[Chemical Formula 26]

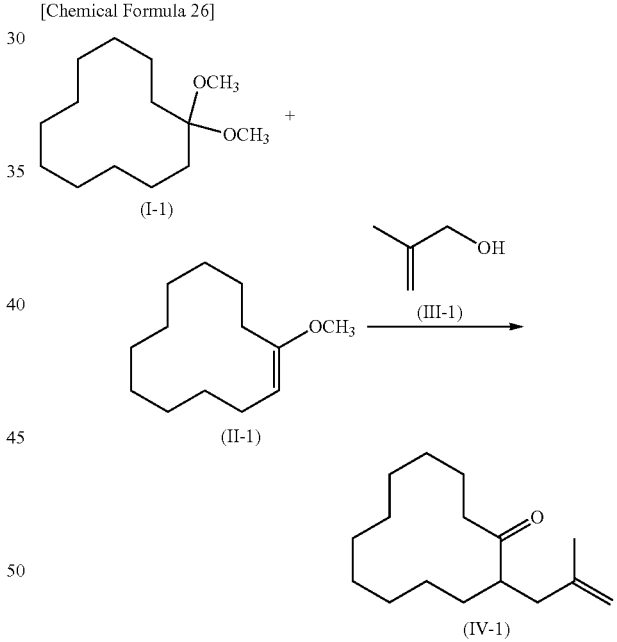

A thermometer, a mechanical stirrer, and a 10-step Sulzer rectification column were installed on a 2-L four-neck flask containing 1,1-dimethoxycyclododecane (I-1) and 1-methoxy-1-cyclododecene (II-1) synthesized in Production Example 1. At room temperature, β-methallyl alcohol (II-1) (296.7 g, 4.115 mol) was added to the four-neck flask. The content in the flask was stirred into a homogeneous system, and then was heated in an oil bath at an outside temperature of 140° C. under nitrogen stream. The top temperature was monitored overtime and was confirmed to be 65° C. After 3.5 hours, it was confirmed if the content in the flask became free of 1,1-dimetoxycyclododecane (I-1) and 1-methoxy-1-cyclododecene (II-1), and then the reaction was stopped.

Next, a K-shaped pipe, a cooling pipe, and a distillate receiver were installed on the 2-L four-neck flask containing the reaction solution (containing 2-(2-methylallyl)cyclododecanone (IV-1)), the reaction solution was heated and stirred at 18.0 kPa and 120° C. to distill off β-methallyl alcohol (III-1) (distilled-off amount: 67.1 g). After the reaction solution was heated and stirred for 2 hours, the pressure was reduced to 16 kPa, and the reaction solution was heated and stirred for another 1 hour in order to complete the distillation.

After β-methallyl alcohol had been distilled off under reduced pressure, the residue was transferred to a 2-L separable reaction container with a jacket, and then alkali water obtained by dissolving $K_2HPO_4$ (0.4 g, 2.057 mmol) in 20.2 g of ion-exchange water was added thereto. A mechanical stirrer, a thermometer, a Dimroth condenser, and a nitrogen-flow device were installed on the separable reaction container. The mixture in the separable reaction container was vigorously stirred at room temperature for 1 hour. After the stirring had been finished, the mixture was heated to 80° C. using a condenser and was then left to stand till layers were separated. An aqueous layer (15.4 g) was removed from the separable reaction container, and then the pH of the residue was checked. The pH was 8.0 (pH test paper).

Simple distillation was performed in order to distill off the residual β-methallyl alcohol (III-1) and water from the residue. AK-shaped pipe, a cooling pipe, and a distillate receiver were installed on the separable reaction container containing the residue, the residue was heated and stirred at 0.3 kPa and 130° C. for 2 hours to distill off β-methallyl alcohol (III-1) and water. Thus, a residue (671.2 g) was obtained. Gas chromatography analysis on the residue revealed that 2-(2-methylallyl)cyclododecanone (IV-1) corresponded to 94.7 GC area %. The yield of 2-(2-methylallyl)cyclododecanone (IV 1) calculated from the amount of 2-(2-methylallyl)cyclododecanone obtained was 99.9%.

Production Example 2

Synthesis of Mixture of 1,1-Dimetoxycyclododecane (I-1) and 1-Methoxy-1-cyclododecene (II-1)

[Chemical Formula 27]

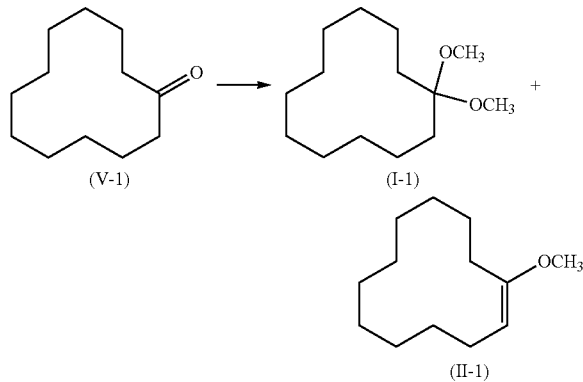

After cyclododecanone (V-1) (500.0 g, 2.743 mol), trimethyl orthoformate (349.3 g, 3.292 mol), and methanol (263.7 g, 8.229 mol) were placed into a 2-L four-neck flask, and the air was purged with nitrogen, the resultant mixture was stirred at room temperature for 4 hours under a nitrogen atmosphere into a homogeneous solution. Pyridinium p-toluenesulfonate (PPTS, 0.7 g, 2.743 mmol) was added thereto, stirred, and dissolved. A Dimroth condenser was attached to the 2-L four-neck flask, and a circulator was used to flow warm water at 37° C. in the Dimroth condenser. A Dean-Stark dewatering pipe was attached to an end of the Dimroth condenser, and a 200-mL distillate receiver was attached to the lower portion of the dewatering pipe. The distillate receiver was immersed in ice water and was thus cooled with ice. Another Dimroth condenser was attached to the upper portion of the Dean-Stark dewatering pipe, and another circulator was used to flow cold water at 10° C. in the Dimroth condenser. One end of a silicone tube was attached to the top of the Dimroth condenser cooled to 10° C., and the other end was introduced to an ethanol-dry ice trap. A portion beyond the trap was sealed with nitrogen. Under a nitrogen atmosphere, the content in the 2-L four-neck flask was heated and refluxed at a bath temperature of 80° C. for 8 hours. As a result of gas chromatography analysis on the reaction end product, the component composition was as follows: 1,1-dimetoxycyclododecane (I-1) corresponded to 93.1 GC area %, 1-methoxy-1-cyclododecene (II-1) corresponded to 6.2 GC area %, and cyclododecanone (V-1) corresponded to 0.8 GC area %.

A K-shaped pipe, a cooling pipe, and a distillate receiver were installed on the 2-L four-neck flask containing the reaction end product. Under a nitrogen atmosphere, the solvent was distilled off from the reaction end product at 101.3 kPa over 4.5 hours while the bath temperature was raised from 100° C. to 120° C. As a result of gas chromatography analysis on the reaction solution after the distillation, the component composition was as follows: 1,1-dimetoxycyclododecane (I-1) corresponded to 25.9 GC area %, 1-methoxy-1-cyclododecene (II-1) corresponded to 73.7 GC area %, and cyclododecanone (V-1) corresponded to 0.3 GC area %.

Example 2

Synthesis of 2-(2-Methylallyl)cyclododecanone

[Chemical Formula 28]

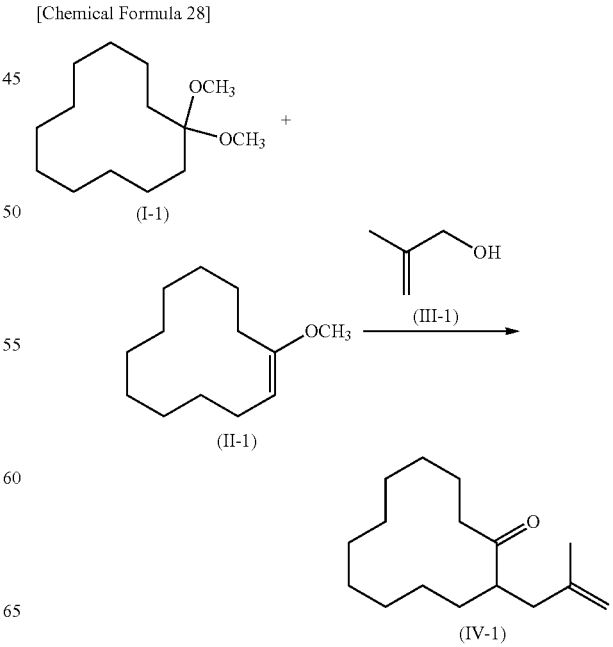

A K-shaped pipe, a cooling pipe, and a distillate receiver were installed on a 2-L four-neck flask containing 1,1-dimetoxycyclododecane (I-1), 1-methoxy-1-cyclododecene (II-1), and cyclododecanone (V-1) synthesized in Production Example 2. β-Methallyl alcohol (III-1) (296.7 g, 4.115 mol) was dripped into the four-neck flask over 8 minutes while the reactants were heated and stirred at a bath temperature of 110° C. under a nitrogen atmosphere. Methanol was distilled off at a bath temperature of 110° C. under nitrogen stream into the four-neck flask till the content of the methallyl cyclododecanone corresponded to 40 to 50 GC area %. After 4 hours, the flow of methanol from the four-neck flask stopped (distilled-off amount: 108.9 g). The K-shaped pipe, the cooling pipe, and the distillate receiver were removed from the four-neck flask, a Dimroth condenser was attached to the four-neck flask, the bath temperature was raised to 130° C., and then the reaction mixture was heated and refluxed for 17 hours.

Next, a K-shaped pipe, a cooling pipe, and a distillate receiver were installed on the 2-L four-neck flask containing the reaction solution, and the reaction solution was heated and stirred at 18.0 kPa and a bath temperature of 120° C. for 3.5 hours to distill off β-methallyl alcohol (III-1) (distilled-off amount: 79.7 g). As a result of gas chromatography analysis on the reaction solution after the distillation, the component composition was as follows: 2-(2-methylallyl)cyclododecanone corresponded to 92.5 GC area %.

Alkali water obtained by dissolving K₂HPO₄ (0.358 g, 2.057 mmol) in 20.0 g of ion-exchange water was added to the 2-L four-neck flask containing the reaction solution after β-methallyl alcohol had been distilled under reduced pressure, and the resultant mixture was vigorously stirred at room temperature for 1 minute. Next, the viscosity of the reaction solution was reduced by raising the bath temperature to 80° C., and then the reaction solution was left to stand for 15 minutes to separate layers. The pH of the aqueous layer of the reaction solution was 8.0 (pH test paper). As a result of gas chromatography analysis on the oil layer of the reaction solution, 2-(2-methylallyl)cyclododecanone (IV-1) corresponded to 92.5 GC area %. The amount of the oil layer obtained was 644.9 g (theoretical amount: 648.5 g). The yield of 2-(2-methylallyl)cyclododecanone (IV-1) calculated from the amount of 2-(2-methylallyl)cyclododecanone obtained was 92.4%.

Production Example 3

Synthesis of Mixture of
1,1-Dimethoxycyclododecane (1-2) and
1-Ethoxy-1-cyclododecene (II-2)

[Chemical Formula 29]

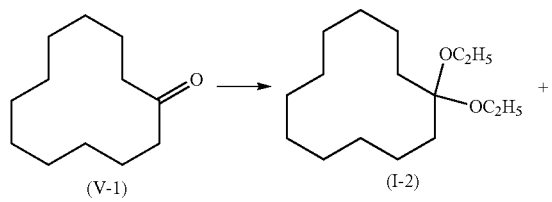

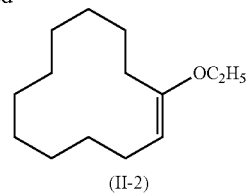

Cyclododecanone (V-1) (4.4 g, 0.024 mol), triethyl orthoformate (8.6 g, 0.058 mol), and ethanol (6.6 g, 0.14 mol were placed into a glass container with a glass side arm (Tokyo Rikakikai Co., Ltd., EYELA: Product No. 212760). Pyridinium p-toluenesulfonate (PPTS, 0.035 g, 0.00014 mmol) was added thereto, stirred, and dissolved. Then, under a nitrogen atmosphere, the resultant mixture was heated and refluxed at a bath temperature of 90° C. for 36 hours.

The reaction solution obtained at the end of the reaction was heated at 101.3 kPa to 165° C. by gradually raising the bath temperature from 100° C. Then, the solvent was distilled off from the four-neck flask over 7 hours. As a result of gas chromatography analysis on the reaction solution after the distillation, the component composition was as follows: 1,1-dietoxycyclododecane (I-2) corresponded to 65.7%, 1-ethoxy-1-cyclododecene (II-2) corresponded to 15.6%, and cyclododecanone (V-1) corresponded to %.

Example 3

Synthesis of 2-(2-Methylallyl)cyclododecanone

[Chemical Formula 30]

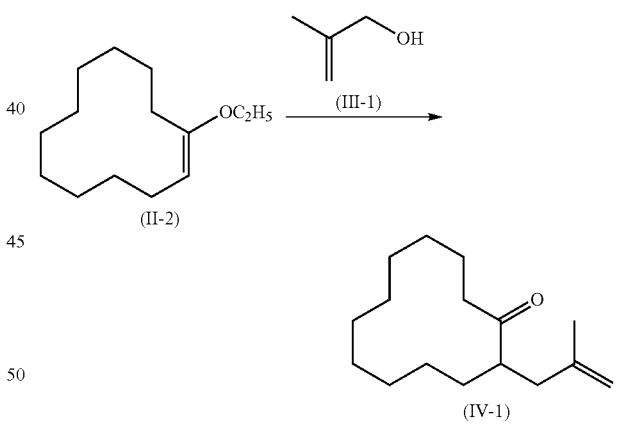

The reaction solution synthesized in Production Example 3 that contained 1,1-diethoxycyclododecane (1-2) in an amount of 65.7%, 1-ethoxy-1-cyclododecene (II-2) in an amount of 15.6%, and cyclododecanone (V-1) in an amount of %, and β-methallyl alcohol (III-1) (5.2 g, 0.072 mol) were placed into a glass container with a glass side arm (Tokyo Rikakikai Co., Ltd., EYELA: Product No. 212760). The resultant mixture was heated at 140° C. for 11 hours. A saturated aqueous solution of sodium hydrogen carbonate (10 ml) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (7.0 g). 2-(2-Methylallyl)cyclododecanone (IV-1) in the reaction end solution corresponded to 79.2 GC area %, and the yield was 92.4%.

Example 4

Synthesis of 2-(2-Methylallyl)cyclododecanone

[Chemical Formula 31]

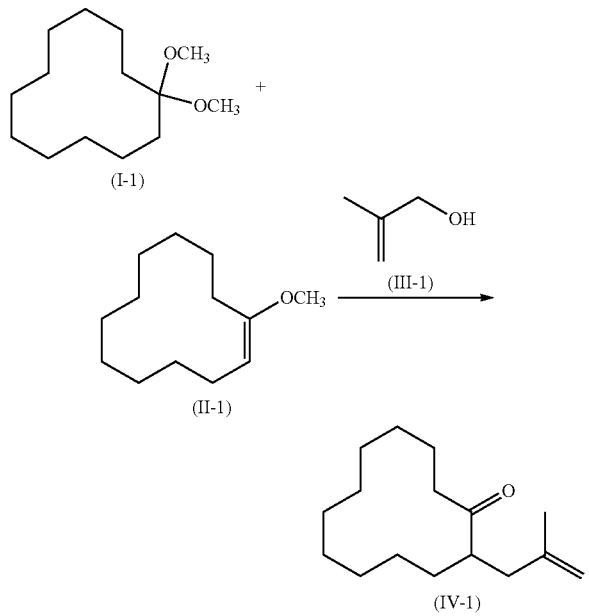

A mixture (6.1 g, 27.0 mmol; manufactured by Symrise AG) containing 1,1-dimetoxycyclododecane (I-1), 1-methoxy-1-cyclododecene (II-1), and cyclododecanone (V-1), β-methallyl alcohol (III-1) (2.6 g, 36.0 mmol), and ammonium chloride (NH$_4$Cl, 0.7 g, 0.13 mmol) were weighed into a glass container with a glass side arm (Tokyo Rikakikai Co., Ltd., EYELA: Product No. 212760), and then heated at 140° C. for 3 hours using Personal Organic Synthesizer (Tokyo Rikakikai Co., Ltd., EYELA: CCX-3200). A saturated aqueous solution of sodium hydrogen carbonate (10 ml) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (6.11 g). 2-(2-Methylallyl)cyclododecanone (IV-1) in the reaction end solution corresponded to 92.3 GC area %, and the yield was 87.9%.

Examples 5 to 7

2-(2-Methylallyl)cyclododecanone (IV-1) was synthesized in the same manner as in Example 4, except that the equivalent of the catalyst (NH$_4$Cl) in Example 4 was changed as listed in Table 3.

Examples 8 to 10

2-(2-Methylallycyclododecanone (IV-1) was synthesized in the same manner as in Example 4, except that the catalyst (NH$_4$Cl) in Example 4 was changed to pyridinium p-toluenesulfonate (PPTS) and the equivalent thereof was changed as listed in Table 3.

Example 11

[Chemical Formula 32]

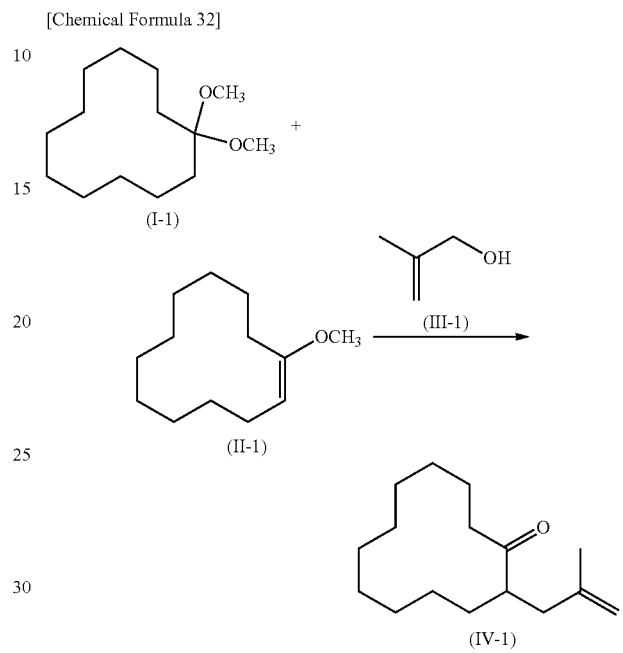

A mixture (3.2 g, 13.8 mmol; manufactured by Symrise AG) containing 1,1-dimetoxycyclododecane (I-1), 1-methoxy-1-cyclododecene (II-1), and cyclododecanone (V-1), β-methallyl alcohol (III-1) (1.4 g, 19.7 mmol), and p-toluenesulfonic acid monohydrate (PTS, 0.0026 g, 0.014 mmol) were weighed into a glass container with a glass side arm (Tokyo Rikakikai Co., Ltd., EYELA: Product No. 212760), and then heated at 140° C. for 2 hours using Personal Organic Synthesizer (Tokyo Rikakikai Co., Ltd., EYELA: CCX-3200). A saturated aqueous solution of sodium hydrogen carbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (3.5 g). 2-(2-Methylallyl)cyclododecanone (IV-1) in the reaction end solution corresponded to 88.7 GC area %, and the yield was 92.9%.

Example 12

Synthesis of 2-(2-Methylallyl)cyclododecanone

[Chemical Formula 33]

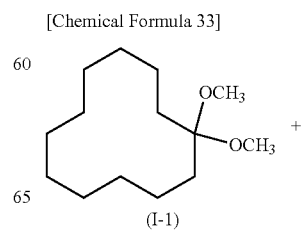

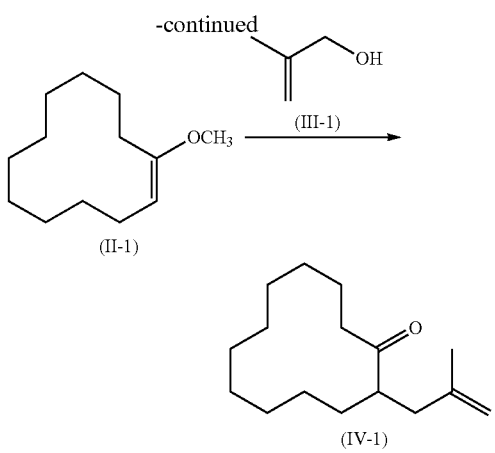

A mixture (6.1 g, 27.0 mmol; manufactured by Symrise AG) containing 1,1-dimetoxycyclododecane (I-1), 1-methoxy-1-cyclododecene (II-1), and cyclododecanone (V-1), β-methallyl alcohol (III-1) (2.6 g, 36.0 mmol), and pyridinium p-toluenesulfonate (PPTS, 0.006 g, 0.024 mmol) were weighed into a glass container with a glass side arm (Tokyo Rikakikai Co., Ltd., EYELA: Product No. 212760), and then heated at 140° C. for 2 hours using Personal Organic Synthesizer (Tokyo Rikakikai Co., Ltd., EYELA: CCX-3200). A saturated aqueous solution of sodium hydrogen carbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (6.7 g). 2-(2-Methylallyl)cyclododecanone (IV-1) in the reaction end solution corresponded to 92.3 GC area %, and the yield was 96.6%.

Comparative Example 1

Synthesis of 2-(2-Methylallyl)cyclododecanone

[Chemical Formula 34]

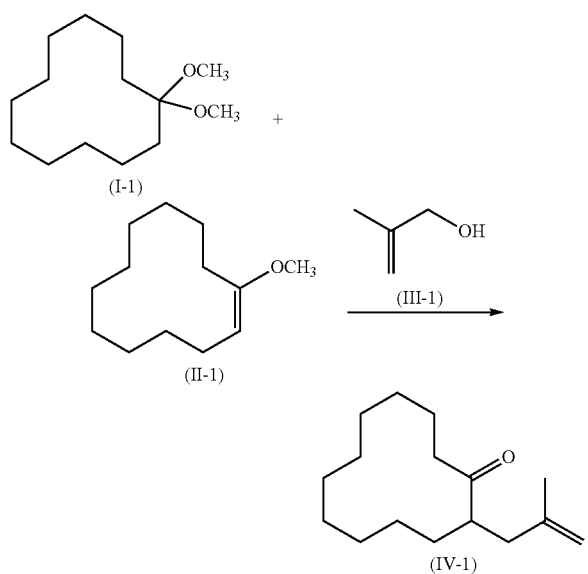

A mixture (6.1 g, 24.1 mmol manufactured by Symrise AG) containing 1,1-dimetoxycyclododecane (I-1), 1-methoxy-1-cyclododecene (II-1), and cyclododecanone (V-1), β-methallyl alcohol (III-1) (3.6 g, 50.0 mmol), and malonic acid (0.003 g, 0.027 mmol, pKa1 2.65, pKa2 5.28) were weighed into a glass container with a glass side arm (Tokyo Rikakikai Co., Ltd., EYELA: Product No. 212760), and then heated at 140° C. for 2 hours using Personal Organic Synthesizer (Tokyo Rikakikai Co., Ltd., EYELA: CCX-3200). A saturated aqueous solution of sodium hydrogen carbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (5.6 g). 2-(2-Methylallyl)cyclododecanone (IV-1) in the reaction end solution corresponded to 27.6 GC area %, and the yield was 24.2%.

Comparative Example 2

Synthesis of 2-(2-Methylallyl)cyclododecanone

[Chemical Formula 35]

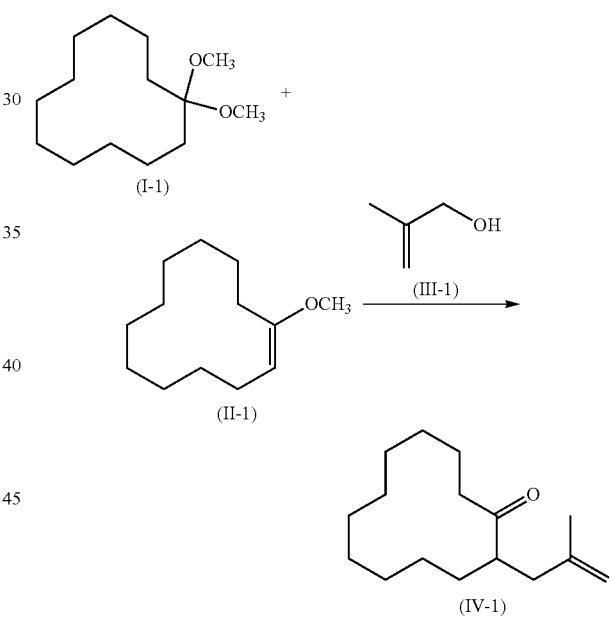

A mixture (6.1 g, 24.1 mmol; manufactured by Symrise AG) containing 1,1-dimetoxycyclododecane (I-1), 1-methoxy-1-cyclododecene (II-1), and cyclododecanone (V1), β-methallyl alcohol (III-1) (3.6 g, 50.0 mm), and propionic acid (0.004 g, 0.047 mmol, pKa 4.67) were weighed into a glass container with a glass side arm (Tokyo Rikakiikai Co., Ltd., EYELA: Product No. 212760), and then heated at 140° C. for 2 hours using Personal Organic Synthesizer (Tokyo Rikakikai Co., Ltd., EYELA: CCX-3200). A saturated aqueous solution of sodium hydrogencarbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (7.4 g). 2-(2-Methylallyl)cyclododecanone (I) in the reaction end solution corresponded to 0.3 GC area %, and the yield was 0.3%.

Table 1 below shows the details of all of the examples and comparative examples above.

TABLE 1

|  | Raw material | Acid catalyst | Equivalent of acid catalyst relative to raw material*1 | Yield of compound of Formula (IV-1)(%) |
|---|---|---|---|---|
| Ex. 1 | Mixture of 1,1-dimetoxycyclododecane (I-1) and 1-methoxy-1-cyclododecene (II-1) | PPTS | 0.001 | 99.9 |
| Ex. 2 | Mixture of 1,1-dimetoxycyclododecane (I-1) and 1-methoxy-1-cyclododecene (II-1) | PPTS | 0.001 | 92.4 |
| Ex. 3 | Mixture of 1,1-dietoxycyclododecane (I-1) and 1-ethoxy-1-cyclododecene (II-1) | PPTS | 0.005 | 92.4 |
| Ex. 4 | Mixture of 1,1-dimetoxycyclododecane (I-1) and 1-methoxy-1-cyclododecene (II-1) | NH$_4$Cl | 0.005 | 87.9 |
| Ex. 5 | Mixture of 1,1-dimetoxycyclododecane (I-1) and 1-methoxy-1-cyclododecenc (II-1) | NH$_4$Cl | 0.1 | 93.4 |
| Ex. 6 | Mixture of 1,1-dimetoxycyclododecane (I-1) and 1-methoxy-1-cyclododecene (II-1) | NH$_4$Cl | 0.05 | 95.1 |
| Ex. 7 | Mixture of 1,1-dimetoxycyclododecane (I-1) and 1-methoxy-1-cyclododecene (II-1) | NH$_4$Cl | 0.005 | 94.1 |
| Ex. 8 | Mixture of 1,1-dimetoxycyclododecane (I-1) and 1-methoxy-1-cyclododecene (II-1) | PPTS | 0.005 | 78.0 |
| Ex. 9 | Mixture of 1,1-dimetoxycyclododecane (I-1) and 1-methoxy-1-cyclododecene (II-1) | PPTS | 0.01 | 74.6 |
| Ex. 10 | Mixture of 1,1-dimetoxycyclododecane (I-1) and 1-methoxy-1-cyclododecene (II-1) | PPTS | 0.1 | 44.5 |
| Ex. 11 | Mixture of 1,1-dimetoxycyclododecane (I-1) and 1-methoxy-1-cyclododecene (II-1) | PTS | 0.001 | 92.9 |
| Ex. 12 | Mixture of 1,1-dimetoxycyclododecane (I-1) and 1-methoxy-1-cyclododecene (II-1) | PPTS | 0.001 | 96.6 |
| Comp. Ex. 1 | Mixture of 1,1-dimetoxycyclododecane (I-1) and 1-methoxy-1-cyclododecene (II-1) | Malonic acid | 0.001 | 24.2 |
| Comp. Ex. 2 | Mixture of 1,1-dimetoxycyclododecane (I-1) and 1-methoxy-1-cyclododecene (II-1) | Propionic acid | 0.002 | 0.3 |

*1"Raw material" means the total of the compound of General Formula (I) and the compound of General Formula (II)

As can be appreciated from Table 1 above, with the method of the present invention, it is possible to obtain a highly pure compound of Formula (IV) in increased yield from a compound of Formula (I) and/or a compound of Formula (II).

INDUSTRIAL APPLICABILITY

With the production method of the present invention, it is possible to produce a highly pure compound of Formula (IV) in increased yield. Furthermore, a compound of Formula (IV) is useful to produce muscenone.

The invention claimed is:

1. A method for producing an α-allylated cycloalkanone represented by Formula (IV), the method comprising
reacting a compound represented by Formula (I) and/or a compound represented by Formula (II) with a compound represented by Formula (III) in the presence of an acid catalyst to produce an α-allylated cycloalkanone represented by Formula (IV),
wherein the acid catalyst includes an acid catalyst that consists of an ammonium cation and an anion

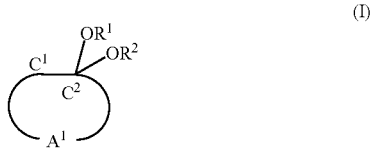

(I)

(II)

(III)

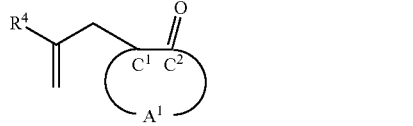

(IV)

where $R^1$, $R^2$, and $R^3$ are the same or different and each of them is an alkyl group having 1 or more and 4 or less of carbon atoms, the group -$A^1$- is an alkylene group having 4 or more and 20 or less of carbon atoms that optionally contains a hetero atom and optionally has a substituent, and where the front bond of the group -$A^1$- refers to a bond that binds to the carbon atom $C^1$ and the back bond of the group -$A^1$- refers to a bond that binds to the carbon atom $C^2$ and $R^4$ is a hydrogen atom or an alkyl group having 1 or more and 4 or less of carbon atoms, the ammonium canon is represented b Formula (X) or Formula (XI);

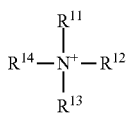

(X)

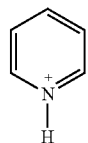

(XI)

where $R^{11}$, $R^{12}$, $R^{13}$, and $R^{14}$ are the same or different and each of them is a hydrogen atom or an alkyl group having 1 or more and 5 or less of carbon atoms, the anion is a sulfonate anion represented by Formula (XII) or a halide ion:

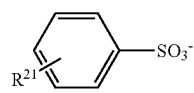

(XII)

where $R^{21}$ is a hydrogen atom or an alkyl group having 1 or more and 5 or less of carbon atoms.

2. The method according to claim 1, wherein the group -$A^1$- is an alkylene group having 10 or more and 14 or less of carbon atoms that optionally has a substituent.

3. The method according to claim 1, wherein the group -$A^1$- is an alkylene group having 10 or more and 12 or less of carbon atoms.

4. The method according to claim 1, wherein an amount of the acid catalyst that is used is $10^{-5}$ equivalents or more and 1 equivalent or less relative to a total amount of the compound of Formula (I) and the compound of Formula (II).

5. The method according to claim 1, wherein the reacting a compound represented by Formula (I) and/or a compound represented by Formula (II) with a compound represented by Formula (III) in the presence of an acid catalyst is performed at a temperature of 120° C. or higher and 150° C. or lower.

6. The method according to claim 1, wherein the reacting is performed using a rectification column.

7. The method according to claim 1, further comprising reacting a compound represented by Formula (V) with an alcohol having 1 or more and 4 or less of carbon atoms in the presence of a second acid catalyst to produce the compound represented by Formula (I) and/or the compound represented by Formula (II),

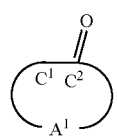

(V)

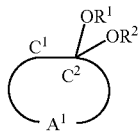

(I)

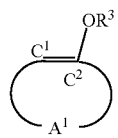

(II)

where $R^1$, $R^2$, and $R^3$ are the same or different and each of them is an alkyl group having 1 or more and 4 or less of carbon atoms, and the group -$A^1$- is an alkylene group having 4 or more and 20 or less of carbon atoms that optionally contains a hetero atom and optionally has a substituent, and where the front bond of the group -$A^1$- refers to a bond that binds to the carbon atom $C^1$ and the back bond of the group -$A^1$- refers to a bond that binds to the carbon atom $C^2$.

8. The method according to claim 7, wherein the second acid catalyst is one or more selected from the group consisting of p-toluenesulfonic acid, montmorillonite, and pyridinium p-toluenesulfonate.

9. The method according to claim 7, wherein the second acid catalyst comprises the catalyst which is the same as the acid catalyst.

10. The method according to claim 7, wherein the group -$A^1$- is an alkylene group having 10 or more and 14 or less of carbon atoms that optionally has a substituent.

11. The method according to claim 7, wherein the group -$A^1$- is an alkylene group having 10 or more and 12 or less of carbon atoms.

12. The method according to claim 7, wherein the reacting of a compound represented by Formula (V) with an alcohol having 1 or more and 4 or less of carbon atoms in the presence of a second acid catalyst is performed at a temperature of 120° C. or higher and 150° C. or lower.

13. The method according to claim 1, wherein the Formula (I) is Formula (I-1) below, the Formula (II) is Formula (II-1) below, and the Formula (IV) is Formula (IV-1) below:

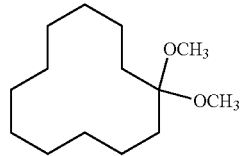

(I-1)

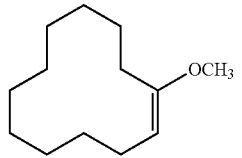

(II-1)

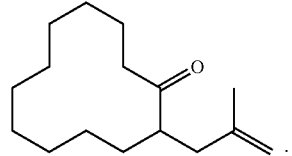

(IV-1)

14. A method for synthesizing muscenone, the method comprising:
reacting a compound represented by Formula (I-1) and/or a compound represented by Formula (II-1) with β-methallyl alcohol in the presence of an acid catalyst to produce an α-allylated cycloalkanone represented by Formula (IV-1), wherein the acid catalyst includes an acid catalyst that consists of an ammonium cation and an anion;
(i) cyclization of the α-allylated cycloalkanone represented by General Formula (IV-1);

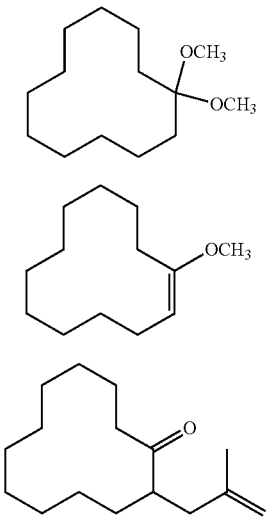

(I-1)

(II-1)

(IV-1)

(ii) hydrogenation;
(iii) oxidative cleavage,
(iv) reduction; and
(v) ring-opening
the ammonium cation is represented by General Formula (X) or Formula (XI);

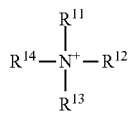

(X)

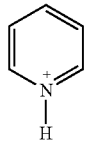

(XI)

where $R^{11}$, $R^{12}$, $R^{13}$, and $R^{14}$ are the same or different and each of them is a hydrogen atom or an alkyl group having 1 or more and 5 or less of carbon atoms, the anion is a sulfonate anion represented by General Formula (XII) or a halide ion:

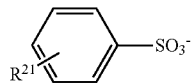

(XII)

where $R^{21}$ is a hydrogen atom or an alkyl group having 1 or more and 5 or less of carbon atoms.

15. The method according to claim 14, wherein an amount of the acid catalyst that is used is $10^{-5}$ equivalents or more and 1 equivalent or less relative to a total amount of the compound of Formula (I-1) and the compound of Formula (II-1).

16. The method according to claim 14, wherein the reacting a compound represented by Formula (I-1) and/or a compound represented by Formula (II-1) in the presence of an acid catalyst is performed at a temperature of 120° C. or higher and 150° C. or lower.

17. The method according to claim 14, wherein the reacting is performed using a rectification column.

* * * * *